(12) United States Patent
Flugge-Berendes et al.

(10) Patent No.: US 8,840,911 B2
(45) Date of Patent: Sep. 23, 2014

(54) MOISTURIZING HAND SANITIZER

(75) Inventors: Lisa Ann Flugge-Berendes, Appleton, WI (US); Scott W. Wenzel, Neenah, WI (US); Corey Thomas Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 406 days.

(21) Appl. No.: 12/044,222

(22) Filed: Mar. 7, 2008

(65) Prior Publication Data
US 2009/0226498 A1 Sep. 10, 2009

(51) Int. Cl.
*A61K 31/045* (2006.01)
*A61K 9/00* (2006.01)
*A61K 8/86* (2006.01)
*A61K 8/39* (2006.01)
*A61K 8/34* (2006.01)
*A61Q 17/00* (2006.01)
*A61K 8/891* (2006.01)
*A61K 8/31* (2006.01)

(52) U.S. Cl.
CPC ............... *A61K 31/045* (2013.01); *A61K 8/86* (2013.01); *A61K 8/39* (2013.01); *A61K 8/34* (2013.01); *A61Q 17/005* (2013.01); *A61K 8/891* (2013.01); *A61K 8/31* (2013.01)
USPC .......................................... 424/411; 514/724

(58) Field of Classification Search
USPC ....................................................... 424/411
See application file for complete search history.

(56) References Cited

U.S. PATENT DOCUMENTS

| | | | |
|---|---|---|---|
| 4,606,913 A * | 8/1986 | Aronson et al. ................. | 424/59 |
| 4,667,890 A | 5/1987 | Gietman, Jr. | |
| 5,540,332 A | 7/1996 | Kopacz et al. | |
| 5,770,183 A * | 6/1998 | Linares ............................ | 424/59 |
| 6,180,214 B1 * | 1/2001 | Nissing et al. ............. | 428/195.1 |
| 6,183,766 B1 | 2/2001 | Sine et al. | |
| 6,228,385 B1 | 5/2001 | Shick | |
| 6,423,329 B1 | 7/2002 | Sine et al. | |
| 6,472,356 B2 | 10/2002 | Narula et al. | |
| 6,617,294 B2 | 9/2003 | Narula et al. | |
| 6,651,924 B2 | 11/2003 | Gingras et al. | |
| 6,685,952 B1 | 2/2004 | Ma et al. | |
| 6,783,766 B2 | 8/2004 | Pate et al. | |
| 6,905,748 B2 | 6/2005 | Sosalla | |
| 7,056,496 B2 | 6/2006 | Pate et al. | |
| 7,144,148 B2 | 12/2006 | Reed et al. | |
| 7,153,902 B2 | 12/2006 | Altes et al. | |
| 2002/0155281 A1 | 10/2002 | Lang et al. | |
| 2003/0069317 A1 | 4/2003 | Seitz et al. | |
| 2004/0235693 A1 | 11/2004 | Wei et al. | |
| 2004/0247685 A1 | 12/2004 | Modak et al. | |
| 2005/0282914 A1 | 12/2005 | Reed et al. | |
| 2006/0008621 A1 | 1/2006 | Gusky et al. | |
| 2006/0217288 A1 * | 9/2006 | Wahl et al. ..................... | 510/515 |
| 2007/0219273 A1 | 9/2007 | Greten et al. | |
| 2007/0276087 A1 | 11/2007 | Paul | |

FOREIGN PATENT DOCUMENTS

| | | |
|---|---|---|
| WO | 02/03925 A1 | 1/2002 |
| WO | 2004098559 A2 | 11/2004 |
| WO | 2006010088 A1 | 1/2006 |
| WO | 2006042180 A1 | 4/2006 |

OTHER PUBLICATIONS

International Search Report and Written Opinion for PCT/IB2009/050603 mailed Sep. 22, 2009.
Extended European Search Report received in EP Patent Application No. 09717091.4, mailed Apr. 29, 2013.

* cited by examiner

*Primary Examiner* — Audrea Buckley
(74) *Attorney, Agent, or Firm* — Armstrong Teasdale LLP

(57) ABSTRACT

The present disclosure generally relates to moisturizing hand sanitizers including alcohols that are effective in killing microorganisms while providing a moisturizing benefit to the user's skin. More particularly, the alcohol-based hand sanitizers include a high internal phase emulsion which allows moisturizers or skin protectants such as emollients and/or silicones to be stably incorporated into the sanitizer.

21 Claims, 1 Drawing Sheet

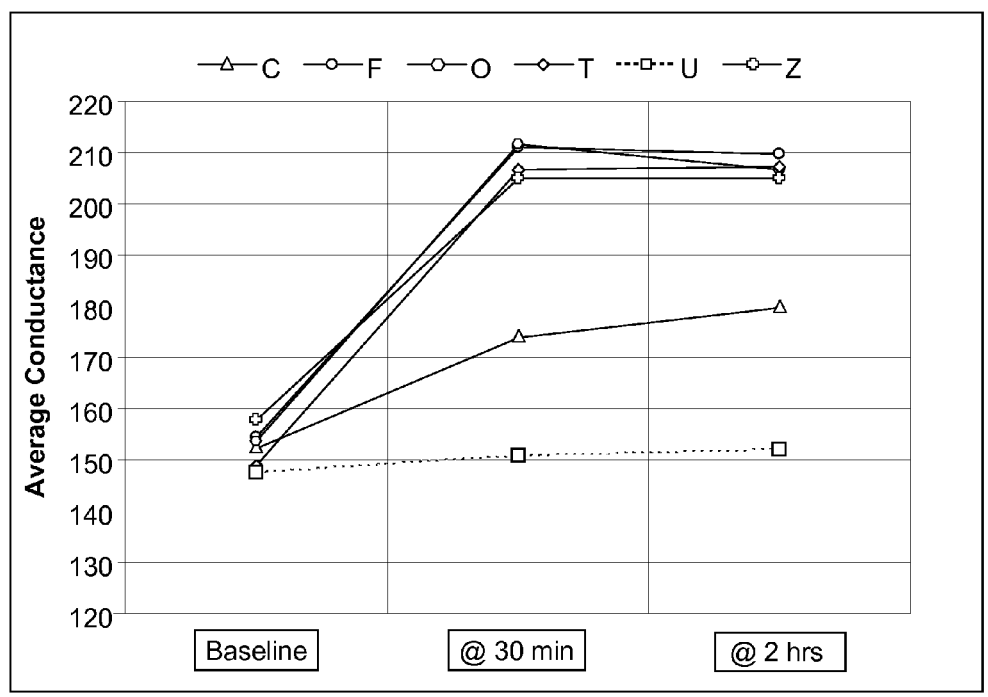

MOISTURIZING HAND SANITIZER

BACKGROUND OF THE DISCLOSURE

The present disclosure generally relates to antimicrobial hand sanitizers including alcohols that are effective in killing microorganisms while providing a moisturizing benefit to the user's skin. More particularly, the alcohol-based hand sanitizers include a high internal phase emulsion which allows moisturizers or skin protectants such as emollients and/or silicones to be stably incorporated into the sanitizer.

The notion of so called "germs" and germ transmission is well known by consumers. One of the best and easiest ways of preventing germ and/or disease transmission is by routinely washing one's hands. Recognizing the inconvenience or impossibility of such hand washing under certain circumstances, such as traveling conditions and/or time constraints, a number of manufacturers have introduced hand sanitizing products which sanitize skin surfaces without the need for water and/or drying towels.

Although alcohol and alcohol-containing sanitizers are known to possess bactericidal activity and to prevent infections, such as methicillin-resistant *Staphylococcus aureus* (MRSA) infections in hospital settings, such sanitizers typically require the use of anywhere from 60% to 95% alcohol, such as ethanol, in order to be effective. Unfortunately, use of ethanol at these levels can be very drying to the skin. As such, continuous use of such products can leave the user's skin dry, often resulting in red, chapped, and cracked skin.

To improve a user's skin, many companies have conventionally included moisturizers, such as humectants, emollients, and the like, as additional components in their alcohol-based hand sanitizers. While lending some protection against drying of the skin, there are several drawbacks to these conventional sanitizers. For instance, conventional sanitizers comprising moisturizers or other hydrophobic skin protectants are unstable and tend to separate over extended periods of time. As a result, the added moisturizers or skin protectants do not remain evenly distributed throughout the sanitizer, rendering the moisturizing ability of the sanitizer ineffective. Additionally, the instability of the sanitizers may cause the formation of large oil layers on the skin and, as a result, the sanitizer may feel greasy and not aesthetically pleasing on the skin. Incorporation of moisturizers or skin protectants, such as emollients, directly into a sanitizer also requires additional processing steps, which adds to the complexity and cost of the manufacturing process.

The present disclosure addresses these problems by providing an alcohol-based hand sanitizer that is stable and provides a moisturizing benefit to the user's skin. In particular, it has been discovered that incorporating a high internal phase emulsion into an alcohol-based moisturizing hand sanitizer provides the sanitizer with stability and superior moisturization, without requiring additional steps during the manufacturing process.

SUMMARY OF THE DISCLOSURE

The present disclosure generally relates to antimicrobial hand sanitizers including alcohols that are effective in killing microorganisms while providing a moisturizing benefit to the user's skin. More particularly, the alcohol-based hand sanitizers include a high internal phase emulsion which allows moisturizers or skin protectants such as emollients and/or silicones to be stably incorporated into the sanitizer.

In one aspect, the present disclosure is directed to a moisturizing hand sanitizer comprising water, an alcohol, and a high internal phase emulsion. The high internal phase emulsion comprises an emulsifier and a skin protectant selected from the group consisting of an emollient, a silicone, and combinations thereof. The high internal phase emulsion comprises an aqueous phase in an amount of about 30% (by weight of the emulsion) or less.

In another aspect, the present disclosure is directed to a wet wipe. The wet wipe comprises a wipe substrate, a moisturizing hand sanitizer. The moisturizing hand sanitizer comprises water, an alcohol, and a high internal phase emulsion. The high internal phase emulsion comprises an emulsifier and a skin protectant selected from the group consisting of an emollient, a silicone, and combinations thereof, wherein the high internal phase emulsion comprises an aqueous phase in an amount of about 30% (by weight of the emulsion) or less.

In another aspect, the present disclosure is directed to a method of making a moisturizing hand sanitizer. The method comprises combining from about 0.1% (by weight of the sanitizer) to about 10% (by weight of the sanitizer) of a high internal phase emulsion, from about 1% (by weight of the sanitizer) to about 90% (by weight of the sanitizer) water, and from about 20% (by weight of the sanitizer) to about 95% (by weight of the sanitizer) of an alcohol to form the sanitizer, wherein the sanitizer is formed at room temperature. The high internal phase emulsion comprises an emulsifier and a skin protectant selected from the group consisting of an emollient, a silicone, and combinations thereof, and the high internal phase emulsion comprises an aqueous phase in an amount of about 30% (by weight of the emulsion) or less.

Other objects and features will be in part apparent and in part pointed out hereinafter.

BRIEF DESCRIPTION OF THE DRAWINGS

FIG. 1 is a chart depicting the average conductance values for various hand sanitizers at baseline, 30 minutes, and 2 hours, as described in Example 3. "U" indicates the untreated test site; "C" indicates the KIMCARE® sanitizer; "Z" indicates the control sanitizer (0% HIPE); "F" indicates Sanitizer 1 (0.5% HIPE); "O" indicates Sanitizer 2 (1.0% HIPE); and "T" indicates Sanitizer 3 (2.0% HIPE).

DETAILED DESCRIPTION OF THE INVENTION

The present disclosure generally relates to antimicrobial hand sanitizers including alcohols that are effective in killing microorganisms while providing a moisturizing benefit to the user's skin. More particularly, the alcohol-based hand sanitizers include a high internal phase emulsion which allows moisturizers or skin protectants such as emollients and/or silicones to be stably incorporated into the sanitizer.

As noted above, conventional hand sanitizers having moisturizers incorporated therein are unstable over extended periods of time. In particular, added moisturizers or skin protectants such as emollients do not remain uniformly distributed throughout the sanitizer, but rather separate out of the sanitizer forming large layers or globules. This instability adversely affects the ability of the sanitizer to provide a moisturizing benefit to the user's skin, as large portions of the sanitizer may comprise no moisturizer. Additionally, instability of moisturizing sanitizers may result in the formation of larger oil layers on the skin when the sanitizer is used. As a result, the sanitizer may feel greasy and not aesthetically pleasing on the skin.

In accordance with the present disclosure it has been discovered that a high internal phase emulsion comprising moisturizers or skin protectants such as emollients and/or silicones can be used in combination with an alcohol-based hand sanitizer to provide a sanitizer having microbiocidal efficacy and good moisturizing effects. Advantageously, by incorporating the moisturizer or skin protectant into the alcohol-based hand sanitizer as part of a high internal phase emulsion, the moisturizer or skin protectant remains substantially stably distributed throughout the sanitizer for extended periods of time, and does not separate out of the sanitizer. As a result, the moisturizing hand sanitizers of the present disclosure have good moisturization effects, are substantially stable over extended periods of time, and have good aesthetics and feel on a user's skin.

Additionally, the moisturization benefits of the hand sanitizers of the present disclosure may be long-lasting. Without wishing to be bound to any particular theory, it is believed that when the sanitizer is applied to a user's hands, the alcohol, water, and other sanitizer components evaporate off the skin, leaving behind the high internal phase emulsion which forms a thin, partially occlusive film on the skin that provides a long-lasting moisturization benefit.

Thus, in one aspect, the present disclosure is directed to a moisturizing hand sanitizer comprising an alcohol, a carrier such as water, and a high internal phase emulsion. The high internal phase emulsion comprises an aqueous phase, a non-aqueous phase, and an emulsifier. The non-aqueous phase may comprise a moisturizer or skin protectant that has moisturizing and/or other skin conditioning properties, such as an emollient and/or a silicone. The moisturizing hand sanitizer may be formulated with a suitable pharmaceutically acceptable carrier into compositions such as lotions, creams, liquids, and the like, that may be applied to skin or mucosa. For example in one particularly preferred embodiment, the moisturizing hand sanitizer is suitably in the form of an instant hand sanitizer.

In another aspect, a moisturizing hand sanitizer of the present disclosure may be used in combination with a product, such as a personal care product. More particularly, the moisturizing hand sanitizer may be incorporated into or onto a substrate, such as a wipe substrate, an absorbent substrate, a fabric or cloth substrate, or a tissue substrate, among others. For example, the moisturizing hand sanitizer may be incorporated into personal care products, such as wipes, absorbent articles, bath tissues, cloths, and the like. In one preferred embodiment, the moisturizing hand sanitizer is a liquid or gel-like composition that may be used in combination with a wipe substrate to form a wet wipe.

The presence of the alcohol in the moisturizing hand sanitizer provides the sanitizer with microbiocidal properties against most bacteria and fungi. More particularly, the alcohol is suitably capable of killing gram-positive and/or gram-negative bacteria, fungi, mold, a variety of viruses, protozoans, parasites, and other microbes. The potent activity of the alcohol against a microorganism is believed to be due to its denaturation of proteins and enzymes and cellular dehydration.

Suitable alcohols for use with the sanitizers of the present disclosure can include any water-soluble alcohol known in the art. Typically, the alcohol will be a short chain alcohol. Non-limiting examples of suitable alcohols include methanol, ethanol, propanol, isopropyl alcohol, butanol, t-butanol, 2-butanol, pentanol, hexanol, or combinations thereof. Typically, the alcohol is ethanol, isopropyl alcohol or combinations thereof. More typically, the alcohol is ethanol. In one embodiment, the alcohol is a specially denatured alcohol, such as SD alcohol 40B.

Typically, the more concentrated the alcohol in the sanitizer, the more potent the antimicrobial effect. However, increasing the alcohol concentration has the deleterious effect of increasing the level of skin irritancy for users of the sanitizer. Suitably, the hand sanitizer of the present disclosure comprises alcohol in an amount of from about 20% (by weight of the sanitizer) to about 95% (by weight of the sanitizer), and more typically in an amount of from about 60% (by weight of the sanitizer) to about 95% (by weight of the sanitizer). In one particular embodiment, the hand sanitizer comprises isopropyl alcohol in an amount of from about 20% (by weight of the sanitizer) to about 95% (by weight of the sanitizer), and more typically in amount of from about 50% (by weight of the sanitizer) to about 91.3% (by weight of the sanitizer).

In addition to the alcohol, in certain embodiments, the hand sanitizer of the present disclosure may optionally further comprise other disinfectants or antimicrobial agents that contribute to the anti-microbial effect of the sanitizer.

Suitable disinfectants include, for example, quaternium compounds, biguanidines, halogenated compounds, and combinations thereof.

In preferred embodiments, the disinfectants are FDA approved or approved for use in the European Union. Examples of suitable FDA approved disinfectants are described in the Tentative Final Monograph for OTC Topical Antimicrobial Products (Federal Register, Jan. 6, 1978, 43 FR 1210: 1211-49, and in the Tentative Final Monograph for Healthcare Antiseptic Drug Products (Federal Register, Jun. 17, 1994, 59 FR 31402, 31402-52), herein incorporated by reference. It should be understood that the specific disinfectants and amounts thereof that are approved for use in the United States or European Union are subject to periodic change. As such, the specific examples and amounts set forth herein are not intended to be limiting.

For example, for a product marketed in the United States, preferred disinfectants and concentrations (reported as a percentage by weight of the sanitizer) may include benzalkonium chloride in amounts from about 0.1% to about 0.13%, benzethonium chloride in amounts from about 0.1% to about 0.2%, methylbenzethonium chloride in amounts up to about 0.5%, hexylresorcinol, chlorhexidine gluconate in amounts up to about 0.5% to about % 4, para-chloro-meta-xylenol in amounts up to about 0.24% to about 3.75%, chloroxylenol in amounts up to about 0.24% to about 3.75%, cloflucarban, fluorosalan, hexachlorophene in amounts up to about 0.1%, iodine complex (ammonium ether sulfate and polyoxyethylene sorbitan monolaurate), iodine complex (phosphate ester of alkylaryloxy polyethylene glycol), iodine tincture U.S.P., iodine topical solution U.S.P., nonylphenoxypoly(ethyleneoxy)ethanolidine, poloaxmer-iodine complex, triple dye, povidone-iodine complex in amounts up to about 5% to about 10%, undecoylium chloride iodine complex, mercufenol chloride, methylbenzethonium chloride, phenol greater than 1.5% aqueous/alcoholic, phenol less than about 1.5%, secondary amyltricresols, sodium oxychlorosene, tribromsalan, triclocarban, triclosan in amounts up to about 1%, calomel/oxyquinoline benzoate/triethanolamine/phenyl derivative combination, and mercufenol chloride/secondary amyltricresols in 50 percent alcohol combinations. Combinations of these disinfectants may also be used. Preferably, the disinfectant is selected from the group consisting of chlorhexidine, chloroxylenol, hexachlorophene, iodine, iodophors, quaternium ammonium compounds such as benzalkonium chloride or benzethonium chloride, triclosan, and combinations thereof.

As noted above, the alcohol present in the hand sanitizer can cause dryness and irritation to the skin of the user, such as chapping and cracking. To help condition and protect the user's skin, the sanitizers of the present disclosure further comprise one or more moisturizer or other skin protectant, such as an emollient and/or a silicone. To avoid the instability that typically occurs when a moisturizer is added to an alcohol-based sanitizer, the sanitizers of the present disclosure advantageously are formulated using a high internal phase emulsion ("HIPE") that comprises an emollient and/or a silicone. By incorporating the moisturizer or skin protectant (e.g., emollient and/or silicone) into the sanitizer as part of a HIPE, the moisturizer or skin protectant does not separate out of the sanitizer. As a result, the sanitizer is substantially stable over extended periods of time.

As used herein, the term "high internal phase emulsion" or "HIPE" is intended to refer to a substantially stable emulsion comprising a non-aqueous phase and an aqueous phase, wherein the high internal phase emulsion comprises the aqueous phase in an amount of about 30% (by weight of the emulsion) or less. Preferably, the HIPE will comprise an aqueous phase in an amount of about 20% (by weight of the emulsion) or less.

The HIPE preferably has a mean droplet size of about 5 microns or less. Without wishing to be bound to any particular theory, it is believed that it is this small droplet size that allows the HIPE (and thus the emollients and/or silicones) to remain suspended throughout the sanitizer for extended periods of time, thus avoiding the problem of sanitizer instability that typically results when emollients and/or silicones are simply added to a sanitizer. Additionally, the small droplets have good skin feel when the sanitizer is applied to a user's skin, and, as such, result in a sanitizer having good aesthetics.

The HIPEs used herein comprise an aqueous phase, at least one non-aqueous phase, and an emulsifier. Typically, the non-aqueous phase will comprise a skin protectant or moisturizer, such as an emollient and/or a silicone. For instance, in one embodiment, the HIPE comprises an emulsifier, an aqueous phase, and an emollient. In another embodiment, the HIPE comprises an emulsifier, an aqueous phase, and a silicone. In yet another embodiment, the HIPE may comprise an emulsifier, an aqueous phase, an emollient, and a silicone. Optionally, other components, such as humectants, botanicals, sunscreens, and the like, may be incorporated into the aqueous and/or non-aqueous phase of the HIPE, depending on their solubility.

As noted above, in one embodiment, the HIPE may comprise an emollient, which typically acts to soften, soothe, and otherwise moisturize the skin. Suitable emollients that can be incorporated into the HIPE of the present disclosure include oils such as petrolatum based oils, petrolatum, vegetable based oils, mineral oils, natural or synthetic oils, lanolin and its derivatives, fatty esters, glycerol esters and derivatives, propylene glycol esters and derivatives, alkoxylated carboxylic acids, alkoxylated alcohols, fatty alcohols, fatty acids, and combinations thereof. Preferably, the emollient is petrolatum.

Suitable esters could include, but not be limited to, cetyl palmitate, stearyl palmitate, cetyl stearate, isopropyl laurate, isopropyl myristate, isopropyl palmitate, and combinations thereof. The fatty alcohols could include, but not be limited to, octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

Suitable natural fats or oils include fats, oils, essential oils, essential fatty acids, non-essential fatty acids, phospholipids, and combinations thereof. These natural fats and oils can provide a source of essential and non-essential fatty acids to those found in the skin's natural barrier. Specific examples of suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, maleated soybean oil, meadowfoam oil, palm kernel oil, peanut oil, rapeseed oil, grapeseed oil, safflower oil, sphingolipids, seed almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, thyme oil, and combinations thereof.

The emollient may be present in the HIPE in an amount of from about 0.01% (by weight of the emulsion) to about 90% (by weight of the emulsion) and more desirably from about 1% (by weight of the emulsion) to about 85% (by weight of the emulsion).

Alternatively, or in addition to an emollient, the HIPE may also comprise other skin protectants, such as a silicone. These materials help improve the barrier properties of the skin and protect them from external irritants or sensitizers.

Suitable silicone materials include, for example, a silicone surfactant, a volatile silicone oil, a non-volatile silicone oil, or combinations thereof. More particularly, the silicone material may be, for example, dimethicone, cyclomethicone, polyalkylsiloxanes, polyarylsiloxanes, polyalkylarylsiloxanes, polysiloxane gums, polyether siloxane copolymers, and combinations thereof. Exemplary silicone and silicone derivatives also include branched or linear cyclical silicone or silicone derivatives, cyclomethicone, dimethicone polysiloxane, dimethiconol, polysiloxanes, polysiloxane copolymers, polyalkyl aryl silanes, polyaryl siloxanes, polyalkyl siloxanes, polyalkyl aryl silanes, polysiloxane copolymers, alkyl dimethicones, alkyl methicones, alkyldimethicone copolyols, phenyl silicones, alkyl trimethylsilanes, cyclopentasiloxane, dimethicone crosspolymer, trisiloxane, and combinations thereof. Preferred examples of silicones include low viscosity dimethicone, phenyl trimethicione, and silicone fluid DC 345 (available from Dow Corning).

In certain embodiments, the silicone material may also be a low molecular weight polydimethylsiloxane compound. These compounds can be either a linear or a cyclic polydimethylsiloxane compound having a viscosity from about 0.5 to about 10 cst (centistokes). The preferred linear polydimethylsiloxane compounds can have a viscosity range from about 0.5 to 10 cst. The preferred volatile polydimethylsiloxanes have a viscosity in the range of about 0.5 to about 6 cst.

A preferred cyclic, low molecular weight polydimethylsiloxane is a cyclomethicone. Suitable cyclomethicones are available commercially under the trade names DOW CORNING 244 Fluid, DOW CORNING 245 Fluid, DOW CORNING 344 Fluid and DOW CORNING 345 Fluid from DOW CORNING Corporation, Midland, Mich., and SILICONE SF-1173 and SILICONE SF-1202 from Momentive Performance Materials, Wilton, Conn.

A preferred linear, low molecular weight, polydimethylsiloxane compound is decamethyltetrasiloxane, available commercially under the trade names DOW CORNING 200 Fluid, having a boiling point of 195° C. DOW CORNING 200 Fluid may have a viscosity from 0.65 cst to 600,000 cst, but preferably has a viscosity of about 350 cst or less. Other linear polydimethylsiloxanes useful for inclusion in the HIPE include octamethyltrisiloxane and decamethylpentasiloxane.

Preferably, the silicone is selected from the group consisting of dimethicone, cyclomethicone, dimethiconol, dimethicone crosspolymer, and trisiloxane. Particularly preferred silicones include the dimethicone DOW CORNING 200 (available from DOW CORNING Corporation, Midland, Mich.), the cyclomethicones DOW CORNING 245 and DOW CORNING 345 (available from DOW CORNING Corporation, Midland, Mich.), the dimethiconols Siltech E-2171 and S-701 (available from Siltech), the dimethicone crosspolymers DOW CORNING 9040, DOW CORNING 9041, DOW CORNING 9045, and DOW CORNING 9546 (all available from DOW CORNING Corporation, Midland, Mich.), and the trisiloxane DOW CORNING 200 Fluid, 1 cSt (available from DOW CORNING Corporation, Midland, Mich.). The silicone material may also be a cetyl dimethicone, such as ABIL Wax 9801, ABIL Wax 9814, or ABIL Wax 9840 (all available from Evonik, Hopewell, Va.).

The silicone may be present in the HIPE in an amount of from about 0.01% (by weight of the emulsion) to about 90% (by weight of the emulsion) and more desirably from about 1% (by weight of the emulsion) to about 85% (by weight of the emulsion).

In certain embodiments, the non-aqueous phase of the emulsion comprises both an emollient and a silicone. In this embodiment, the HIPE will preferably comprise from about 0.01% (by weight of the emulsion) to about 90% (by weight of the emulsion) of the emollient, and from about 0.01% (by weight of the emulsion) to about 90% (by weight of the emulsion) of the silicone. In one particular embodiment, the non-aqueous phase comprises both petrolatum and dimethicone.

Optionally, the non-aqueous phase of the emulsion may comprise other lipophilic components including, for example, oils, sunscreens, various skin benefit agents, and the like.

As noted above, the HIPE incorporated into the sanitizers of the present disclosure further comprises an aqueous phase. As noted above, the HIPE comprises the aqueous phase in an amount of about 30% (by weight of the emulsion) or less. Typically, the HIPE will contain an aqueous phase in an amount of from about 0.01% (by weight of the emulsion) to about 30% (by weight of the emulsion), and more typically from about 0.1% (by weight of the emulsion) to about 25% (by weight of the emulsion). In certain embodiments, the aqueous phase may comprise only water. Optionally, however, the aqueous phase may additionally comprise certain water soluble ingredients such as humectants, botanicals, and other water-soluble skin benefit agents. Examples of suitable humectants are described hereinafter.

The high internal phase emulsions further comprise at least one emulsifier. Typically, emulsifiers are molecules with non-polar and polar regions that are able to reside at the interface of the water and oil components of the emulsion.

Emulsifiers according to the present disclosure are not particularly limited and will preferably have a hydrophilic/lipophilic balance (HLB) of from 2 to 25, and behave as water-in-oil emulsifiers or oil-in-water emulsifiers. Any suitable emulsifier may be included in the HIPE of the present disclosure including carbon based emulsifiers, silicon based emulsifiers, non-ionic emulsifiers, cationic emulsifiers, and combinations thereof. Suitable carbon based emulsifiers include sorbitan laurate, sorbitan palmitate, sorbitan stearate, sorbitan oleate, sorbitan sesquioleate, sorbitan trioleate, sorbitan isostearate, isoceteth-20, PEG-40 sorbitan peroleate, PEG-40 hydrogenated castor oil, laureth-4, laureth-23, ceteth-2, ceteth-10, ceteth-20, steareth-2, steareth-10, steareth-20, oleth-2 oleth-10, oleth-20, steareth-21, laureth-23, PEG-8 stearate, PEG-20 stearate, glyceryl stearate, hydrogenated vegetable glycerides phosphate, polyglyceryl-3-diisostearate, polyglyceryl-4 oleate, poloxamer 335, or combinations thereof. In one particularly preferred embodiment, the emulsifier is selected from the group consisting of ceteth-10, steareth-21, poloxamer 335, and combinations thereof.

The emulsifier is typically present in the HIPE in an amount of from about 0.01% (by weight of the emulsion) to about 20% (by weight of the emulsion), preferably from about 0.1% (by weight of the emulsion) to about 15% (by weight of the emulsion), and more preferably from about 0.5% (by weight of the emulsion) to about 10% (by weight of the emulsion).

Suitable methods for preparing high internal phase emulsions are known in the art, such as use of high pressure/high shear mixing conditions. For example, the non-aqueous phase may be combined with the aqueous phase and processed under high pressure, high shear, or high pressure/high shear conditions until a HIPE is produced that has a mean droplet size of about 5 microns or less. Any suitable equipment may be used to form the high internal phase emulsion including, for example, homogenizers, microfluidizers, ultrasonic mixers, and the like. Methods of preparing HIPEs are described in U.S. Pat. No. 6,783,766 to Pate, et al., U.S. Pat. No. 7,056,496 to Pate, et al., U.S. Pat. No. 7,144,148 to Reed, et al., U.S. Pat. No. 7,153,902 to Altes, et al., and U.S. Patent Application Publ. No. 2007/0276087 to Paul, et al., all herein incorporated by reference to the extent they are consistent herewith.

Suitable high internal phase emulsions are also commercially available. Non-limiting examples of commercially available HIPEs include:

(1) Dow Corning® 7-3099 dimethicone HIP emulsion. This HIPE includes dimethicone (100 cSt) (80% active) in the non-aqueous phase and ceteth-10 and laureth-4 as the emulsifiers. As used herein the term "% active" means the percent by weight of the emulsion that is not water.

(2) Dow Corning® 7-3100 Gum Blend HIP Emulsion. This HIPE includes cyclopentasiloxane and dimethiconol (84% active) in the non-aqueous phase, and laureth-4 and laureth-23 as the emulsifiers.

(3) Dow Corning® 7-3101 Elastomer Blend HIP Emulsion. This HIPE includes cyclopentasiloxane, dimethicone crosspolymer, and dimethicone (85% active) in the non-aqueous phase and laureth-4 and laureth-23 as the emulsifiers.

(4) Dow Corning® 7-3105 Petrolatum HIP Emulsion. This HIPE includes petrolatum (81% active) in the non-aqueous phase, and ceteth-10, steareth-21, and poloxamer 335 as the emulsifiers.

(5) Dow Corning® 7-3111 Petrolatum Blend HIP Emulsion. This HIPE includes petrolatum and dimethicone (77% active) in the non-aqueous phase, and ceteth-10, steareth-21, and poloxamer 335 as the emulsifiers.

(6) Dow Corning® 7-3110 Volatile Fluid HIP Emulsion. This HIPE includes dimethicone and trisiloxane (80% active) in the non-aqueous phase, and ceteth-10 and laureth-4 as the emulsifiers.

The high internal phase emulsions may be present in the sanitizers of the present disclosure in an amount of from about 0.1% (by weight of the sanitizer) to about 10% (by weight of the sanitizer), and more typically in an amount of from about 0.25% (by weight of the sanitizer) to about 5% (by weight of the sanitizer).

As noted above, in addition to acting as a disinfectant, the hand sanitizers of the present disclosure may also be formulated to provide additional skin health benefits to a user, such as soothing, anti-irritation, and moisturization effects. For instance, the sanitizer can contain additional moisturizers such as humectants, carriers, dyes, fragrances, chelating agents, rheology modifiers, thickeners, pH modifiers, and various other optional components.

In one embodiment, the hand sanitizer further comprises a humectant. Humectant present in the sanitizer may advantageously be deposited on the skin upon use of the sanitizer, thus helping to maintain lipids and essential oils present in the skin. Particular examples of suitable humectants include glycerin, glycerin derivatives, sodium hyaluronate, hyaluronic acid, betaine, amino acids, glycosaminoglycans, honey, sorbitol, glycols such as propylene glycol, polyols, sugars, hydrogenated starch hydrolysates, salts of PCA such as sodium PCA, lactic acid, lactates, urea, and the like. A particularly preferred humectant is glycerin.

The sanitizer of the present disclosure may suitably include one or more humectant in an amount of from about 0.01% (by weight of the sanitizer) to about 10% (by weight of the sanitizer), more desirably in an amount of from about 0.1% (by weight of the sanitizer) to about 5% (by weight of the sanitizer). Optionally, the sanitizer may further comprise moisturizers other than humectants in amounts up to about 5% (by weight of the sanitizer).

The moisturizing hand sanitizer compositions of the present disclosure may further comprises a carrier material such as water. Typically, the water is present in the sanitizer in an amount of from about 1% (by weight of the sanitizer) to about 90% (by weight of the sanitizer). It should be noted that the aqueous phase of the high internal phase emulsion, described above, may also comprise water. Any water present in the HIPE is in addition to the water separately added to the sanitizer as a carrier.

The sanitizers may further comprise a fragrance. Any suitable fragrance may be used. Typically, the fragrance is present in the sanitizer in an amount of from about 0% (by weight of the sanitizer) to about 5% (by weight of the sanitizer, and more typically in an amount of from about 0.01% (by weight of the sanitizer) to about 3% (by weight of the sanitizer). In one preferred embodiment, the fragrance will have a clean, fresh, and/or neutral scent to create an appealing delivery vehicle for the end consumer.

In general, the pH of the sanitizer may be controlled to be within any desired range, depending on the target soil. For use on a human body, it is typically desirable to have a sanitizer with a neutral pH. If necessary, various pH modifiers may be utilized in the sanitizer to achieve the desired pH level. Any suitable acid or alkali material may be used as a pH modifier. For instance, some examples of basic pH modifiers that may be used in the sanitizer include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. Other examples of suitable basic pH modifiers include tris amino 40% (available from Angus Chemical Company), AMP-95 (aminomethylpropanol) (available from Angus Chemical Company), triisopropanolamine (available from Dow Chemical Company), diisopropanolamine (available from Dow Chemical Company), Neutrol® TE (tetrahydroxypropylethylenediamine) (available from BASF), and Ethomeen® C-25 (PEG-15 cocoamine) (available from Akzo Nobel).

Moreover, some examples of acidic pH modifiers that may be used in the present disclosure include, but are not limited to, mineral acids; and carboxylic acids; and polymeric acids.

Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, and alginic acid.

Typically, the pH modifier is present in the sanitizer in an amount of from about 0% (by weight of the sanitizer) to about 5% (by weight of the sanitizer), and more typically in an amount of from about 0.1% (by weight of the sanitizer) to about 3% (by weight of the sanitizer).

Optionally, one or more viscosity enhancers, such as thickeners, may be added to the sanitizer to increase the viscosity of the sanitizer. Suitable viscosity enhancers include clays and derivatives thereof, silicates, silicas and derivatives thereof, and combinations thereof. Suitable clays and derivatives thereof include, but are not limited to, bentonite and derivatives thereof such as quaternium-18 bentonite, hectorite and derivatives thereof such as quaternium-18 hectorite, montmorillonite, and combinations thereof. Suitable silicates include, but are not limited to, magnesium aluminum silicate, sodium magnesium silicate, lithium magnesium silicate, tromethamine magnesium aluminum silicate, and combinations thereof. Suitable silicas and derivatives thereof include, but are not limited to, silica, hydrated silica, hydrophobic silica, silica silylate, silica methyl silylate, colloidal silicone dioxide, fumed silica, and combinations thereof.

Other examples of suitable viscosity enhancers include polyolefin resins, lipophilic/oil thickeners, ethylene/vinyl acetate copolymers, polyethylene, cetyl hydroxy ethyl cellulose, hydroxyethylcellulose, hydroxypropyl methylcellulose, hydroxypropylcellulose, other organically modified celluloses, PVP/decane copolymer, PVM/MA decadiene crosspolymer, PVP/eicosene copolymer, PVP/hexadecane copolymer, butylated PVP, carbomers, acrylic based thickeners, polyethylene glycol 600, polyethylene glycols, myristyl alcohol, cetyl alcohol, stearyl alcohol, behenyl alcohol, PEG-150 distearate, PEG-175 diisostearate, polyglyceryl-10 behenate/eicosadioate, disteareth-100 IPDI, polyacrylamidomethylpropane sulfonic acid, silicone crosspolymers, polyamide blends, and combinations thereof.

The sanitizers may desirably include one or more viscosity enhancers in an amount of from about 0% (by weight of the sanitizer) to about 20% (by weight of the sanitizer, more typically in amounts of from about 0.01% (by weight of the sanitizer) to about 15% (by weight of the sanitizer), and more typically in amounts of from about 0.05% (by weight of the sanitizer) to about 10% (by weight of the sanitizer).

The moisturizing hand sanitizer can also include various preservatives to increase the shelf life of the sanitizer. Some suitable preservatives that can be used in the present disclosure include, but are not limited to, Kathon CG, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative present in the sanitizer can generally vary depending on the relative amounts of the other components present within the sanitizer. For example, in some embodiments, the preservative is present in the sanitizer in an amount between about 0.001% (by weight of the sanitizer) to about 5% (by weight of the sanitizer), in some embodiments between about 0.001% (by weight of the sanitizer) to about 1% (by weight of the sanitizer), and in some embodiments, between about 0.01% (by weight of the sanitizer) to about 1% (by weight of the sanitizer).

In one embodiment, the sanitizer may additionally include one or more sequestrant or chelating agent. The sequestrant may act to enhance preservative efficacy, and bind metals that could discolor the sanitizer or hinder sanitizer stability. In particular, water often contains metal ions, such as calcium ions, that might react with anionic components (e.g., surfactants, acids, etc.) present within the sanitizer.

Some examples of sequestrants that may be used in the sanitizer of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

Typically, when one or more sequestrants are used in the sanitizer, the sanitizer includes the sequestrants in an amount of from about 0.01% (by weight of the sanitizer) to about 2.0% (by weight of the sanitizer). More suitably, the sanitizer includes from about 0.05% (by weight of the sanitizer) to about 1.0% (by weight of the sanitizer) sequestrant.

The sanitizers of the present disclosure may further comprise skin conditioning agents that may help the skin retain moisture, improve softness, or improve texture. Skin conditioning agents include, for example, amino acids, including alanine, serine, and glycine; allantoin, keratin, and methyl glucose dioleate; alpha-hydroxy acids, including lactic acid and glycolic acid, which act by loosening dead skin cells from the skin's surface; other moisturizers (agents that add or hold water in dry skin) including echinacea (an extract of the coneflower plant) and shea butter; exfoliation agents; lubricants; skin-firming agents; anti-callous agents; anti-acne agents; anti-aging agents; anti-wrinkle agents; anti-dandruff agents; anti-irritants; anti-redness agents such as aloe extract; anti-inflammatory agents; skin health benefit agents; wound care agents; skin lipids; enzymes; scar care agents; powders; botanical extracts; vitamins; minerals; sunscreens; surfactants; drugs; quaternary ammonium compounds; and the like.

In one particular embodiment, the skin conditioning agent is a cationic compound such as a quaternium salt, polyquaternium, quaternium, quaternium hectorite (e.g., quaternium-18 hectorite), silicone quaternium materials, cationic surfactant, or combination thereof. One particularly preferred example is a quaternary ammonium compound, such as a quaternary ammonium salt.

Examples of cationic quaternary ammonium salts include, but are not limited to conventionally known monoalkyl quaternary ammonium salts, dialkyl quaternary ammonium salts, and tetra-alkyl quaternary ammonium salts, such as:

(1) Acyclic quaternary ammonium salts having at least two $C_8$ to $C_{30}$, and preferably $C_{12}$ to $C_{22}$ alkyl or alkenyl chains, such as: dimethyl ditallow ammonium methylsulfate, di(hydrogenated tallow)dimethyl ammonium methylsulfate, distearyldimethyl ammonium methylsulfate, dicocodimethyl ammonium methylsulfate, and the like. In one embodiment, the skin conditioning agent is a water insoluble quaternary ammonium material which comprises a compound having two $C_{12}$ to $C_{18}$ alkyl or alkenyl groups connected to the molecule via at least one ester link. In another embodiment, the quaternary ammonium material has two ester links present.

(2) Cyclic quaternary ammonium salts of the imidazolinium type such as di(hydrogenated tallow)dimethyl imidazolinium methyl sulfate, 1-ethylene-bis(2-tallow-1-methyl) imidazolinium methyl sulfate, and the like.

(3) Diamido quaternary ammonium salts such as: methyl-bis(hydrogenated tallow amidoethyl)-2-hydroxethyl ammonium methyl sulfate, methyl bi(tallowamidoethyl)-2-hydroxypropyl ammonium methylsulfate, and the like.

(4) Biodegradable quaternary ammonium salts such as N,N-di(tallowoyl-oxy-ethyl)-N,N-dimethyl ammonium methyl sulfate, and N,N-di(tallowoyl-oxy-propyl)-N,N-dimethyl ammonium methyl sulfate.

Suitable polyquaterniums for use in the moisturizing hand sanitizers include Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-21, Polyquaternium-22, Polyquaternium-23, Polyquaternium-24, Polyquaternium-25, Polyquaternium-26, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-38, Polyquaternium-39, Polyquaternium-40, Polyquaternium-41, Polyquaternium-42, Polyquaternium-43, Polyquaternium-44, Polyquaternium-45, Polyquaternium-46, Polyquaternium-47, Polyquaternium-48, Polyquaternium-49, Polyquaternium-50, Polyquaternium-51, Polyquaternium-52, Polyquaternium-53, Polyquaternium-54, Polyquaternium-55, Polyquaternium-56, Polyquaternium-57, Polyquaternium-58, Polyquaternium-59, Polyquaternium-60, Polyquaternium-61, Polyquaternium-62, Polyquaternium-63, Polyquaternium-64, Polyquaternium-65, Polyquaternium-66, Polyquaternium-67, Polyquaternium-68, Polyquaternium-69, Polyquaternium-70, Polyquaternium-71, Polyquaternium-72, Polyquaternium-73, Polyquaternium-74, Polyquaternium-75, Polyquaternium-76, and Polyquaternium-79.

Suitable quaterniums include Quaternium-8, Quaternium-14, Quaternium-15, Quaternium-16, Quaternium-18, and Quaternium-80.

Other suitable cationic compounds include silicone quaternium materials, such as silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-17, silicone quaternium-18, silicone quaternium-19, silicone quaternium-20, and silicone quaternium-21.

Suitable cationic surfactants for use in the moisturizing hand sanitizers of the present disclosure include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearalkonium chloride, distearalkonium chloride, chlorohexidine diglutamate, polyhexamethylene biguanide (PHMB), cetyl pyridinium chloride, benzammonium chloride, benzalkonium chloride, and combinations thereof.

Other examples of suitable quaternary ammonium compounds include behentrimonium methosulfate, cetrimonium chloride, cocamidopropyl pg-dimonium chloride, guar hydroxypropyltrimonium chloride, isostearamidopropyl morpholine lactate, quaternium-18 hectorite, quaternium-79 hydrolyzed silk, quaternium-79 hydrolyzed soy protein, rape seed amidopropyl ethyldimonium ethosulfate, cetyl triethylmonium dimethicone PEG-8 succinate, palmitamidopropyltrimonium chloride, butylglucosides, hydroxypropyltrimonium chloride, laurdimoniumhydroxypropyl decylglucosides chloride, and the like.

Other suitable cationic compounds for use in the hand sanitizing compositions of the present disclosure include those cationic compounds listed in International Cosmetic Ingredient Dictionary and Handbook, 11$^{th}$ Edition (2006) and in 2007 Cosmetic Bench Reference, available on-line at http://www.CosmeticBenchReference.com, both of which are incorporated by reference herein to the extent they are consistent herewith.

The amount of skin conditioning agent in the sanitizer is not particularly limited and is typically present in an amount of from about 0% (by weight of the sanitizer) to about 10% (by weight of the sanitizer, more typically from about 0.01% (by weight of the sanitizer) to about 10% (by weight of the sanitizer), preferably from about 0.5% (by weight of the sanitizer) to about 8% (by weight of the sanitizer), and more preferably from about 1% (by weight of the sanitizer) to about 5% (by weight of the sanitizer).

In order to better enhance the sanitizer, other optional ingredients can also be used. For instance, some classes of ingredients that can be used include, but are not limited to: anti-microbial agents, antioxidants (product integrity); astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); hydrotropes (helps dissolve some anti-microbial agents); opacifiers (reduce the clarity or transparent appearance of the product); skin exfoliating agents (ingredients that increase the rate of skin cell turnover such as alpha hydroxy acids and beta hydroxyacids); dyes or colorants; and the like.

As noted above, the moisturizing hand sanitizers of the present disclosure advantageously provide an enhanced moisturizing effect, while maintaining good aesthetics and skin feel and remaining substantially stable over extended periods of time. Typically, the sanitizers will remain substantially stable (i.e., the emollient and/or silicone added as part of the HIPE do not precipitate out of the sanitizer or form large aggregate droplets) for at least about 2 months at room temperature, preferably for at least about 1 year at room temperature, and more preferably for at least about 2 years at room temperature. Alternately, the sanitizers will remain substantially stable for at least about 2 months at 40° C.

Preparation of Sanitizers

The moisturizing hand sanitizers of the present disclosure may be prepared by combining the high internal phase emulsion with the other sanitizer components at room temperature and mixing. Because the emollients and/or silicones are added to the sanitizer as part of the high internal phase emulsion, heating and other expensive or time consuming processing steps are not required to obtain a homogenous final stable sanitizer composition. In addition to moisturizing hand sanitizers, the high internal phase emulsions described herein may also be used to form other stable alcohol based personal care formulations.

Thus, in one embodiment, the present disclosure is directed to a method of making a moisturizing hand sanitizer or other stable alcohol-based personal care formulation. The method comprises combining a high internal phase emulsion, as described herein, with water and an alcohol and mixing. Typically, the sanitizer or other personal care formulation is mixed for from about 5 minutes to about 30 minutes. As noted above, such a formulation may advantageously be formed at room temperature (e.g., from about 20° C. to about 30° C.), and does not require additional processing steps to obtain a homogenous mixture. Optionally, however, the sanitizer or other personal care formulation may be formed at temperatures above room temperature, if desired. Formulation components may be added in any suitable amount, as described herein.

The order in which formulation components are combined to form the sanitizer or other personal care formulation is not critical. In one embodiment, the high internal phase emulsion is combined with water to form a dispersion, and the alcohol is then added to the dispersion to form the sanitizer or personal care formulation. In other embodiments, the alcohol and water are combined to form a dispersion, and the high internal phase emulsion then added to the alcohol/water dispersion. Optionally, additional formulation components may be combined with the water, alcohol, and high internal phase emulsion at various points during processing, depending on their solubility and function in the composition. For instance, in one embodiment, a humectant may be combined with the water and/or alcohol prior to or after combining the water and/or alcohol with the high internal phase emulsion. In another embodiment, a viscosity enhancer may be added to the formulation prior to or after other formulation components have been added or combined to adjust the formulation viscosity to the desired level. For example, the viscosity enhancer can be added to the alcohol, water, and/or humectant prior to or after combining the alcohol, water, and/or humectant with the high internal phase emulsion.

Personal Care Products

In another aspect, the moisturizing hand sanitizers of the present disclosure may be used in combination with a product, such as a personal care product. More particularly, the sanitizer may be incorporated into or onto a substrate, such as a wipe substrate, an absorbent substrate, a fabric or cloth substrate, or a tissue substrate, among others. For example, the compositions may be incorporated into personal care products, such as wipes, absorbent articles, bath tissues, cloths, and the like. More particularly, the moisturizing hand sanitizer may be incorporated into wipes such as wet wipes, hand wipes, face wipes, cosmetic wipes, and the like, or absorbent articles, such as diapers, training pants, adult incontinence products, feminine hygiene products, and the like, and combinations thereof. In one preferred embodiment, the moisturizing hand sanitizer is a liquid composition that may be used in combination with a wipe substrate to form a wet wipe or may be a wetting composition for use in combination with a dispersible wet wipe. In another embodiment, the moisturizing hand sanitizer can be used in combination with a wipe substrate, which is packaged together with one or more absorbent articles, such as diapers.

Although discussed primarily in terms of a wetting composition for use in a wet wipe, it should be understood that the moisturizing hand sanitizers described herein can also be used in combination with numerous other personal care products, such as those described above.

Thus, in one particularly preferred embodiment, the moisturizing hand sanitizer is incorporated into a wetting composition for use in a wet wipe.

The wet wipe may comprise a nonwoven material that is wetted with an aqueous solution termed the "wetting composition," which may also comprise the moisturizing hand sanitizer disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5-10 and a length of about 6-15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

Wetting Composition

The wetting composition for use in combination with the nonwoven materials may desirably comprise the moisturizing hand sanitizer of the present disclosure. As noted above, the moisturizing hand sanitizer has efficacy against a broad spectrum of microorganisms. As such, the antimicrobial wetting composition will help keep microbiological and fungal growth in the wet wipe at an acceptable level.

The wetting composition may include a variety of additives or components, including those disclosed in U.S. Patent Publication No. 2002/0155281, which is incorporated herein in its entirety. Possible additives may include, but are not limited to skin-care additives, odor control additives, wetting agents and/or cleaning agents; water, emollients, surfactants, fragrances, preservatives, chelating agents, pH buffers, or combinations thereof as are well known to those skilled in the art. Further, the wetting agent may also contain lotions, medicaments, and/or other antimicrobials.

Relative to the weight of the dry substrate, the wet wipe may desirably contain from about 10 percent to about 600 percent of the wetting composition by weight, more desirably from about 50 percent to about 500 percent of the wetting composition by weight, even more desirably from about 70 percent to about 400 percent of the wetting composition by weight.

Method of Making Wet Wipes

The wetting composition may be applied to the fibrous material by any known process. Suitable processes for applying the wetting composition include, but are not limited to printing, spraying, electrostatic spraying, the use of metered press rolls or impregnating. The amount of wetting composition may be metered and distributed uniformly onto the fibrous material or may be non-uniformly distributed onto the fibrous material.

For ease of application, the wetting composition may be applied to the fibrous material in combination with a solvent, as a solution or mixture. A variety of solvents may be used, including, for example, water, methanol, ethanol, acetone, or the like, with water being the preferred solvent. The amount of wetting composition in the solvent may vary, depending on a variety of factors, including the identity and physical characteristics of the fibrous material to which the wetting composition is being applied. Desirably, the mixture or solution of the wetting composition may contain up to about 50 percent by weight of wetting composition solids. More desirably, the wetting composition or mixture may contain from about 10 to 30 percent by weight of wetting composition solids. Even more desirably, the wetting composition or mixture may contain about 12 to 25 percent by weight wetting composition solids.

Once the wetting composition is applied to the fibrous material, drying, if necessary, may be achieved by any conventional means. Once dry, the nonwoven material may exhibit improved tensile strength when compared to the tensile strength of the untreated wet-laid or dry-laid fibrous material.

The finished wet wipes may be individually packaged, desirably in a folded condition, in a moisture proof envelope or packaged in containers holding any desired number of sheets in a water-tight package with a wetting composition applied to the wipe. Some example processes which can be used to manufacture folded wet wipes are described in U.S. Pat. Nos. 5,540,332 and 6,905,748, which are incorporated by reference herein to the extent they are consistent herewith. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (San Jose, Calif.); Shimizu Manufacturing (Japan), and the devices disclosed in U.S. Pat. No. 4,667,890. The U.S. Pat. No. 6,651,924 also provides examples of a process for producing coreless rolls of wet wipes.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this example, moisturizing hand sanitizers of the present disclosure were prepared. The ingredients and amounts used to prepare each hand sanitizer are set forth in Table 1.

TABLE 1

| INCI Name | Sanitizer 1 (wt. %) | Sanitizer 2 (wt. %) | Sanitizer 3 (wt. %) |
| --- | --- | --- | --- |
| Glycerin | 2.00 | 2.00 | 2.00 |
| Hydroxypropylcellulose | 0.05 | 0.05 | 0.05 |
| Water | 31.35 | 30.85 | 29.85 |
| Carbomer | 0.41 | 0.41 | 0.41 |
| *Aloe barbadensis* leaf powder | 0.01 | 0.01 | 0.01 |
| Panthenol | 0.10 | 0.10 | 0.10 |
| SD alcohol 40-B | 65.23 | 65.23 | 65.23 |
| Tocopheryl acetate | 0.10 | 0.10 | 0.10 |
| Aminomethyl propanol | 0.13 | 0.13 | 0.13 |
| Fragrance | 0.12 | 0.12 | 0.12 |
| Petrolatum, dimethicone, ceteth-10, steareth-21, poloxamer 335 | 0.50 | 1.00 | 2.00 |

The sanitizers were prepared by stirring the water and carbomer for 10 to 20 minutes. During this time, half of the glycerin was combined with the hydroxypropylcellulose and aloe powder and mixed for 10 minutes. This glycerin mixture was stirred into the water mixture, and the remainder of the glycerin was added. The resulting mixture was stirred for 30 minutes. While mixing, a high internal phase emulsion (HIPE) comprising petrolatum/dimethicone/ceteth-10/steareth-21/poloxamer 335 (Dow Corning® 7-3111) was added and allowed to disperse. The panthenol, SD alcohol 40-B, tocopheryl acetate, and fragrance were then added. The aminomethyl propanol was then added with stirring, resulting in gelling of the sanitizer composition.

Example 2

In this example, Sanitizers 1 and 2, prepared in Example 1, were evaluated for their effect on skin moisturization. A control hand sanitizer containing the same composition ingredients as the hand sanitizers prepared in Example 1, except having 31.85 wt. % water and none of the petrolatum/dimethicone/ceteth-10/steareth-21/poloxamer 335 high internal phase emulsion (HIPE) was also tested. The commercially available hand sanitizer KIMCARE® Moisturizing Instant Hand Sanitizer (available from Kimberly-Clark Corporation) was also tested. The KIMCARE® Moisturizing Instant Hand Sanitizer had a similar composition to the hand sanitizers prepared in Example 1, except instead of the HIPE, the KIMCARE® sanitizer comprised 1.80 wt. % of Polytrap 6500 (available from AMCOL Health & Beauty Solutions, Inc.).

Six (6) subjects were recruited for this study. Individuals with abnormal skin pigmentation at the test sites, skin disease, skin damage, skin damage due to sun exposure, tattoos or bruises on the testing areas of the arms, or excessive dryness or erythema were excluded. The subjects were instructed not to use skin creams, oils, ointment, powders, perfumes, or lotions on their forearms less than 24 hours prior to and during testing, and to refrain from bathing, showering, or swimming for two hours prior to testing.

On the day of testing, the subjects were acclimated to a temperature and humidity controlled room (23°±2° C.; 50%±5% relative humidity) for 15 minutes prior to baseline testing. During equilibration, three 3 cm×3 cm sites were demarcated on the volar aspect of each subject's forearms. After equilibration, baseline measurements were taken for skin moisture (conductance).

Baseline conductance measurements were taken at the marked test sites using a DermaLab Moisture Flat Probe (Cortex Technology, Hadsund Denmark). Conductance is the cosmetic industry standard for measuring moisture in the skin. The DermaLab Moisture Flat Probe was used for all measurements. It uses electrodes arranged as concentric rings to send a series of alternating electrical currents through the skin. Resistance to the currents indicates the water binding capacity of the stratum corneum, or moisture level, and provides a conductance reading. A higher conductance reading indicates a higher level of moisture in the skin. The instrument's probe was placed at the test site on the subject's forearm and 5 second continuous measurements were taken in triplicate.

At the conclusion of baseline measurements, 50 μL of a hand sanitizer, either Sanitizer 1 or Sanitizer 2 prepared in Example 1 and containing 0.5 wt. % or 1.0 wt. % of the HIPE, respectively, the control hand sanitizer containing 0 wt. % of the HIPE, or the commercially available KIMCARE® Moisturizing Instant Hand Sanitizer, was applied with a positive displacement pipette to a test site. Each test site received a different sanitizer according to a randomization schedule. The sanitizers were rubbed into the test site for approximately 10 seconds using a finger covered by a finger cot. Each sanitizer was tested on each test subject for a total of 6 trials for each sanitizer. The sanitizers were allowed to dry for 30 minutes, and conductance readings were retaken at each test site in triplicate.

Subjects were allowed to leave the test site after the 30 minute reading. Final conductance measurements were taken 120 minutes after application of the sanitizers. Prior to final conductance measurements, the subjects were reacclimated to the temperature and humidity controlled environment for fifteen minutes, as previously described. Final conductance measurements were taken in triplicate at each test site, as described above. The results at 30 and 120 minutes as compared to baseline are shown in Tables 2-5 below. A "**" denotes a difference from baseline at 90% confidence, while "*" denotes a difference from baseline at 95% confidence.

TABLE 2

KIMCARE ® Moisturizing Instant Hand Sanitizer

| Test Subject | Baseline | 30 minute reading | 120 minute reading |
|---|---|---|---|
| A | 143 | 173 | 150 |
| B | 127 | 107 | 93 |
| C | 120 | 240* | 236* |
| D | 40 | 33 | 60 |
| E | 240 | 223 | 283 |
| F | 67 | 87 | 153* |

TABLE 3

Control Sanitizer (0% HIPE)

| Test Subject | Baseline | 30 minute reading | 120 minute reading |
|---|---|---|---|
| A | 170 | 277* | 233* |
| B | 93 | 127 | 110 |
| C | 137 | 207* | 213* |
| D | 57 | 123* | 160* |
| E | 240 | 270 | 267 |
| F | 107 | 170* | 220* |

TABLE 4

Sanitizer 1 (0.5% HIPE)

| Test Subject | Baseline | 30 minute reading | 120 minute reading |
|---|---|---|---|
| A | 143 | 306* | 260* |
| B | 83 | 123* | 87 |
| C | 147 | 227* | 237* |
| D | 47 | 87** | 77 |
| E | 100 | 130 | 127 |
| F | 130 | 197 | 240** |

TABLE 5

Sanitizer 2 (1.0% HIPE)

| Test Subject | Baseline | 30 minute reading | 120 minute reading |
|---|---|---|---|
| A | 143 | 253* | 230* |
| B | 127 | 170* | 153** |
| C | 117 | 123 | 113 |
| D | 37 | 47** | 57* |
| E | 153 | 183 | 177 |
| F | 73 | 97** | 133* |

All of the sanitizers showed significant changes from baseline. Analysis of variance (ANOVA) analysis of the average change from baseline indicates that all the sanitizers are statistically equivalent.

The results indicate that Sanitizer 1 (0.5 wt. % HIPE), Sanitizer 2 (1.0 wt. % HIPE), and the control sanitizer (0% HIPE) performed as well as or better than the commercially available sanitizer KIMCARE® Moisturizing Instant Hand Sanitizer.

Example 3

In this example, Sanitizer 1 (0.5 wt. % HIPE), Sanitizer 2 (1.0 wt. % HIPE), and Sanitizer 3 (2.0 wt. % HIPE), prepared in Example 1, were evaluated for their effect on skin moisturization. The control hand sanitizer described in Example 2 (0 wt. % HIPE) and the commercially available hand sanitizer KIMCARE® Moisturizing Instant Hand Sanitizer (available from Kimberly-Clark Corporation) were also tested.

The moisturization test was performed as described in Example 2, except twenty-three (23) subjects were recruited for the study. Each participant was treated with all 5 of the sanitizers plus one untreated site.

Change from baseline moisture conductance measurements were analyzed using analysis of variance (ANOVA). The results are shown in Table 6 and FIG. 1. FIG. 1 illustrates the average conductance values for the untreated test site and each sanitizer at baseline, 30 minutes, and 120 minutes (2 hours).

TABLE 6

| | 30 Minutes | | 120 Minutes | |
|---|---|---|---|---|
| Treatment | Average change | SG | Average change | SG |
| Untreated | 3.6 | C | 4.7 | D |
| KIMCARE ® Sanitizer | 21.4 | B | 27.4 | C |
| Control (0% HIPE) | 46.8 | A | 47.1 | B |
| Sanitizer 1 (0.5 wt. % HIPE) | 56.9 | A | 52.8 | AB |
| Sanitizer 2 (1.00 wt. % HIPE) | 58.0 | A | 55.4 | AB |
| Sanitizer 3 (2.00 wt. % HIPE) | 58.3 | A | 58.7 | A |

The "Average change" column indicates the average change in conductance from baseline for each treatment group at either 30 minutes or 120 minutes. The "SG" column indicates which codes are significantly different from each other. Codes which do not share the same letter are significantly different at the 95% confidence level.

As can be seen from these results, all sanitizers resulted in a significant increase in the average conductance at 30 minutes and at 120 minutes, relative to the baseline. The untreated site was not significantly different than the baseline conductance measurement at any point.

The results indicate an increasing trend in conductance as a function of amount of the HIPE included in the sanitizers. However, the majority of this increase is the result of inclusion of 0.5 wt. % of the HIPE. The impact of increasing the amount of HIPE to 1.00 wt. % or 2.00 wt. % is small at 30 minutes but statistically significant improvement is seen at 2.00 wt. % at the 2 hour time point.

Example 4

In this example, the stability of a sanitizer of the present disclosure is compared to the stability of a sanitizer that does not comprise a high internal phase emulsion.

Sanitizer 1 (0.5% HIPE), Sanitizer 2 (1.0% HIPE), and Sanitizer 3 (2.0% HIPE) were prepared as described in Example 1. A sanitizer (Sanitizer 4) was also prepared that comprised the same components in amounts similar to those used to prepare Sanitizers 1, 2, and 3, except instead of adding the petrolatum, dimethicone, ceteth-10, steareth-21, and poloxamer 335 to the sanitizer as part of a high internal phase emulsion, these sanitizer ingredients were added separately to the sanitizer, as described below. The ingredients and amounts used to prepare the Sanitizer 4 are set forth in Table 7.

TABLE 7

| INCI Name | Sanitizer 4 (wt. %) |
|---|---|
| Glycerin | 2.00 |
| Hydroxypropylcellulose | 0.05 |
| Water | 29.36 |
| Carbomer | 0.41 |
| Aloe barbadensis leaf powder | 0.01 |
| Panthenol | 0.10 |
| SD alcohol 40-B | 65.23 |
| Tocopheryl acetate | 0.10 |
| Aminomethyl propanol | 0.13 |
| Fragrance | 0.12 |
| Petrolatum | 1.125 |
| Dimethicone | 1.125 |
| Ceteth-10 | 0.09 |
| Steareth-21 | 0.09 |
| Poloxamer 335 | 0.06 |

Sanitizer 4 was prepared by combining water and the carbomer with stirring. The aloe powder was then added. Concurrently, the hydroxypropylcellulose was added to half the glycerin with stirring, stirred for 15 minutes, and added to the water mixture. The container was then rinsed with the remainder of the glycerin which was then added to the water mixture. The resultant mixture was heated to 65° C. with stirring. The petrolatum, dimethicone, ceteth-10, steareth-21, and poloxamer 335 were combined and heated to 65° C. with stirring, then added to the water phase and allowed to cool with stirring. When at room temperature, the panthenol, alcohol, and tocopheryl acetate were added, followed by the aminomethyl propanol.

Sanitizers 1-4 were subjected to one freeze-thaw cycle, and the stability of the sanitizers was observed. Sanitizers 1-3, which comprised either 0.5%, 1.0% or 2.0% by weight, respectively, of the high internal phase emulsion, all maintained their stability (i.e., the petrolatum and dimethicone components were not observed to separate out of the sanitizer) after the freeze-thaw cycle. In contrast, the dimethicone and petrolatum present in Sanitizer 4 (which did not contain a HIPE) separated out of the sanitizer composition after the freeze-thaw cycle. These results indicate that alcohol-based sanitizers comprising skin protectants such as petrolatum and dimethicone added as part of a high internal phase emulsion have superior stability to alcohol-based hand sanitizers comprising petrolatum and dimethicone that have not been added as part of a high internal phase emulsion.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A moisturizing hand sanitizer comprising water, an alcohol, and a high internal phase emulsion, the high internal phase emulsion comprising an emulsifier and a skin protectant selected from the group consisting of an emollient, a silicone, and combinations thereof, wherein the high internal phase emulsion comprises an aqueous phase in an amount of 30% (by weight of the emulsion) or less and the high internal phase emulsion is present in the sanitizer in an amount of from 0.1% (by weight of the sanitizer) to 10% (by weight of the sanitizer).

2. The sanitizer of claim 1 wherein the alcohol is present in the sanitizer in an amount of from 20% (by weight of the sanitizer) to 95% (by weight of the sanitizer).

3. The sanitizer of claim 1 wherein the alcohol is selected from the group consisting of methanol, ethanol, propanol, isopropyl alcohol, butanol, t-butanol, 2-butanol, pentanol, hexanol, and combinations thereof.

4. The sanitizer of claim 1 further comprising a humectant.

5. The sanitizer of claim 4 wherein the humectant is present in the sanitizer in an amount of from 0.1% (by weight of the sanitizer) to 10% (by weight of the sanitizer).

6. The sanitizer of claim 4 wherein the humectant is selected from the group consisting of glycerin, sodium hyaluronate, hyaluronic acid, betaine, amino acids, glycosaminoglycans, honey, sorbitol, glycols, propylene glycol, polyols, sugars, hydrogenated starch hydrolysates, sodium PCA, lactic acid, lactates, urea, and combinations thereof.

7. The sanitizer of claim 1 wherein the high internal phase emulsion is present in the sanitizer in an amount of from 0.25% (by weight of the sanitizer) to 5% (by weight of the sanitizer).

8. The sanitizer of claim 1 wherein the emollient is selected from the group consisting of petrolatum, petrolatum based oils, vegetable based oils, mineral oils, natural or synthetic oils, lanolin, fatty esters, glycerol esters, propylene glycol esters, alkoxylated carboxylic acids, alkoxylated alcohols, fatty alcohols, fatty acids, and combinations thereof.

9. The sanitizer of claim 1 wherein the emollient is present in the high internal phase emulsion in an amount of from 0.01% (by weight of the emulsion) to 90% (by weight of the emulsion).

10. The sanitizer of claim 1 wherein the emulsifier is present in the high internal phase emulsion in an amount of from 0.01% (by weight of the emulsion) to 20% (by weight of the emulsion).

11. The sanitizer of claim 1 wherein the silicone is selected from the group consisting of dimethicone, cyclomethicone, polyalkylsiloxanes, polyarylsiloxanes, polyalkylarylsiloxanes, polysiloxane gums, polyether siloxane copolymers, dimethicone polysiloxane, dimethiconol, polysiloxanes, polysiloxane copolymers, polyalkyl aryl silanes, polyaryl siloxanes, polyalkyl siloxanes, polyalkyl aryl silanes, polysiloxane copolymers, alkyl dimethicones, alkylmethicones, alkyldimethicone copoloyls, phenyl silicones, alkyl trimethylsilanes, dimethicone crosspolymer, trisiloxane, and combinations thereof.

12. The sanitizer of claim 1 wherein the silicone is present in the high internal phase emulsion in an amount of from 0.01% (by weight of the emulsion) to 90% (by weight of the emulsion).

13. The sanitizer of claim 1 wherein the emollient is petrolatum and the silicone is selected from the group consisting of dimethicone, cyclopentasiloxane, dimethiconol, dimethicone crosspolymer, and trisiloxane.

14. The sanitizer of claim 1 further comprising a component selected from the group consisting of a disinfectant, a viscosity enhancer, a fragrance, a pH modifier, a skin conditioning agent, and combinations thereof.

15. The sanitizer of claim 1 wherein the sanitizer comprises from 1% (by weight of the sanitizer) to 90% (by weight of the sanitizer) water, from 20% (by weight of the sanitizer) to 95% (by weight of the sanitizer) of the alcohol, and from 0.01% (by weight of the sanitizer) to 10% (by weight of the sanitizer) of a humectant.

16. The sanitizer of claim 1 wherein the high internal phase emulsion has a mean droplet size of 5 microns or less.

17. A wet wipe comprising:
a wipe substrate, and
a moisturizing hand sanitizer comprising water, an alcohol, and a high internal phase emulsion, the high internal phase emulsion comprising an emulsifier and a skin protectant selected from the group consisting of an emollient, a silicone, and combinations thereof, wherein the high internal phase emulsion comprises an aqueous phase in an amount of 30% (by weight of the emulsion) or less and the high internal phase emulsion is present in the sanitizer in an amount of from 0.1% (by weight of the sanitizer) to 10% (by weight of the sanitizer).

18. The wet wipe of claim 17, wherein the sanitizer comprises from 1% (by weight of the sanitizer) to 90% (by weight of the sanitizer) water and from 20% (by weight of the sanitizer) to 95% (by weight of the sanitizer) of the alcohol.

19. The wet wipe of claim 17 further comprising from 0.01% (by weight of the sanitizer) to 10% (by weight of the sanitizer) of a humectant.

20. A method of making a moisturizing hand sanitizer, the method comprising
combining from 0.1% (by weight of the sanitizer) to 10% (by weight of the sanitizer) of a high internal phase emulsion, from 1% (by weight of the sanitizer) to 90% (by weight of the sanitizer) water, and from 20% (by weight of the sanitizer) to 95% (by weight of the sanitizer) of an alcohol to form the sanitizer,
wherein the high internal phase emulsion comprises an emulsifier and a skin protectant selected from the group consisting of an emollient, a silicone, and combinations thereof, and wherein the high internal phase emulsion comprises an aqueous phase in an amount of 30% (by weight of the emulsion) or less, and
wherein the sanitizer is formed at room temperature.

21. The method of claim 20 further comprising combining from 0.01% (by weight of the sanitizer) to 10% (by weight of the sanitizer) of a humectant with the water, the alcohol, and the high internal phase emulsion.

* * * * *